United States Patent
Lee et al.

(10) Patent No.: US 7,128,442 B2
(45) Date of Patent: Oct. 31, 2006

(54) ILLUMINATION UNIT WITH A SOLID-STATE LIGHT GENERATING SOURCE, A FLEXIBLE SUBSTRATE, AND A FLEXIBLE AND OPTICALLY TRANSPARENT ENCAPSULANT

(76) Inventors: Kian Shin Lee, 2373 KG Selamat 13300 Tasek Gelugor, S.P.U., Penang (MY); Janet Bee Yin Chua, 1-G Lintang Paya Terubung 6, Air Itam, 11500 Penang (MY); Wen Ya Ou, F-0-11, Flat Uda, Tanjung Tokong, 10470 Penang (MY); Yew Cheong Kuan, 8-5-4 Desa University, Jalan Sungai Dua, 11700 Penang (MY)

( * ) Notice: Subject to any disclaimer, the term of this patent is extended or adjusted under 35 U.S.C. 154(b) by 172 days.

(21) Appl. No.: 10/760,763

(22) Filed: Jan. 20, 2004

(65) Prior Publication Data

US 2004/0223328 A1    Nov. 11, 2004

Related U.S. Application Data

(63) Continuation-in-part of application No. 10/434,818, filed on May 9, 2003, now Pat. No. 6,860,620.

(51) Int. Cl.
*F21V 17/06* (2006.01)

(52) U.S. Cl. ........................ 362/278; 362/561; 362/570

(58) Field of Classification Search ................ 362/561, 362/570, 97, 547, 320, 330, 373, 278
See application file for complete search history.

(56) References Cited

U.S. PATENT DOCUMENTS

| | | | | | |
|---|---|---|---|---|---|
| 3,821,847 | A | * | 7/1974 | Melse et al. | 29/827 |
| 5,285,352 | A | * | 2/1994 | Pastore et al. | 361/707 |
| 5,362,679 | A | * | 11/1994 | Wakefield | 29/827 |
| 5,399,903 | A | * | 3/1995 | Rostoker et al. | 257/666 |
| 5,698,866 | A | * | 12/1997 | Doiron et al. | 257/99 |
| 6,045,575 | A | * | 4/2000 | Rosen et al. | 607/88 |
| 6,290,713 | B1 | | 9/2001 | Russell | |
| 6,641,284 | B1 | * | 11/2003 | Stopa et al. | 362/240 |
| 6,743,249 | B1 | * | 6/2004 | Alden | 607/88 |
| 6,806,658 | B1 | * | 10/2004 | Tan et al. | 315/291 |
| 2003/0179548 | A1 | * | 9/2003 | Becker et al. | 361/704 |

* cited by examiner

*Primary Examiner*—Ali Alavi
*Assistant Examiner*—Hargobind S. Sawhney

(57) ABSTRACT

An illumination unit includes a thin and flexible substrate and flexible electrical tracks formed on the flexible substrate. A number of solid-state light generating sources are arranged on the flexible substrate along the electrical tracks and are electrically connected to the electrical tracks. A flexible and optically transparent encapsulant is provided to encapsulate the light generating sources on the substrate such that the illumination unit is both thin and flexible.

21 Claims, 4 Drawing Sheets

US 7,128,442 B2

ILLUMINATION UNIT WITH A SOLID-STATE LIGHT GENERATING SOURCE, A FLEXIBLE SUBSTRATE, AND A FLEXIBLE AND OPTICALLY TRANSPARENT ENCAPSULANT

This application is a continuation-in-part of U.S. patent application Ser. No. 10/434,818, filed May 9, 2003, now U.S. Pat. No. 6,860,620.

TECHNICAL FIELD

The invention relates to an illumination unit. More particularly, the present invention relates to a thin and flexible illumination unit that includes a solid-state light generating source, a flexible substrate, and a flexible and optically transparent encapsulant.

BACKGROUND

Light Emitting Diodes (LEDs) are one type of solid-state light generating devices that have found their way in lighting applications, display applications, photo-therapeutic applications, and other applications where a compact, low voltage, rugged, and high efficiency light source is advantageous. In many such applications, a number of LEDs are arranged into an array or other pre-determined arrangement having similar or dissimilar LED types.

In display applications, LEDs emitting in the red, green, and blue colors are closely packed to form a color "pixel" that blends the three colors. In this manner white light can be generated. Alternatively, by selectively varying the optical output intensity of the three colored LEDs, a selected color can be generated. An array of such "pixels" can form a color display or an illuminating surface emitting white light. In lighting or photo-therapeutic applications, an illumination unit or panel containing LEDs arranged in an array can be formed.

The LEDs can also emit only red, blue or green color, not from the combination of the red, green and blue dies as stated above, but having the individual dies on the package itself emitting the different specific colors.

However, several hurdles remain in the use of LEDs in those applications. One problem associated with the prior LED illumination panel or display is its thickness. This means that the unit must be of the appropriate thickness. For example, a relatively thick LED illumination unit typically affects the therapeutic effectiveness of the unit due to reduced optical intensity. On the other hand, patient safety and comfort may be adversely affected if the unit is made too thin.

The other problem is the rigidity (i.e., not flexible to be bent) of the prior LED illumination unit. As is known, many of the above mentioned applications require that the illumination unit to be flexible. For example, in the lighting application where the LED illumination unit is used as a vehicle lamp, the illumination unit needs to be flexible or soft enough to form a desired shape or contour to follow the contour of a vehicle lamp. In the photo-therapeutic applications, the unit must be flexible enough so that it can follow the contour of the human body part in order to provide safe but effective phototherapy to that body part.

Therefore, what is needed is a thin, flexible, and safe illumination unit.

SUMMARY

One feature of the present invention is to provide an illumination unit having a solid-state light generating source, a flexible substrate, and a flexible and optically transparent encapsulant.

In accordance with one embodiment of the present invention, an illumination unit is provided that includes a thin and flexible substrate and flexible electrical tracks formed on the flexible substrate. A number of solid-state light generating sources are arranged on the flexible substrate along the electrical tracks and are electrically connected to the electrical tracks. A flexible and optically transparent encapsulant is provided to encapsulate the light generating sources on the substrate such that the illumination unit is both thin and flexible.

DETAILED DESCRIPTION

Figure 1:
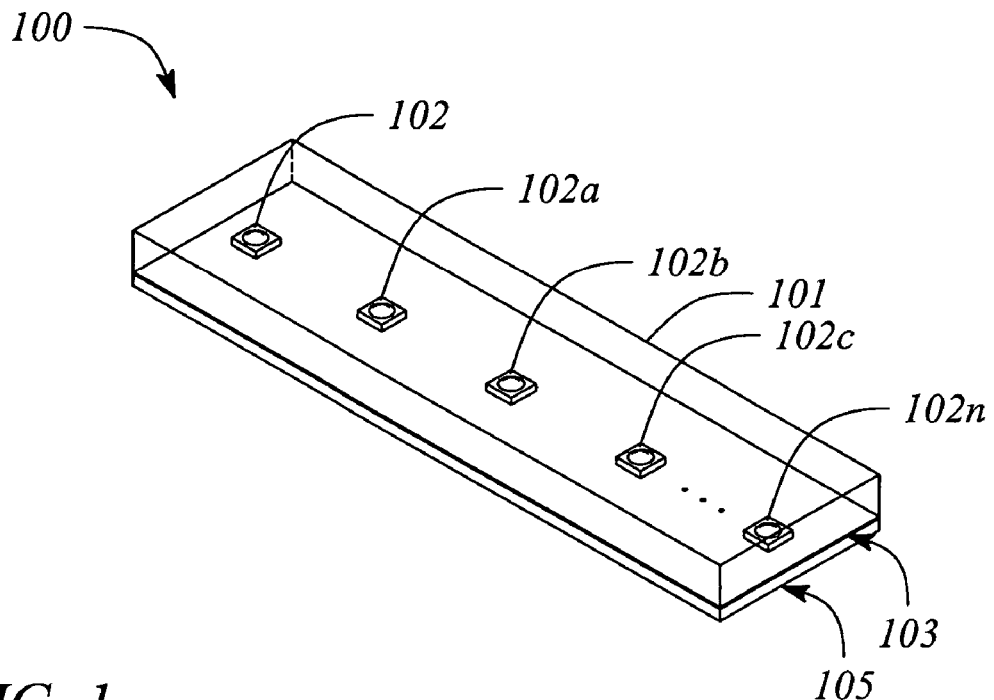
FIG. 1 shows a perspective view of an illumination unit according to one embodiment of the invention.

FIG. 1 shows an illumination unit 100 that implements one embodiment of the present invention. In accordance with one embodiment of the present invention, the illumination unit 100 includes a number of solid-state light generating sources (e.g., light generating sources 102 through 102n) arranged on a thin and flexible substrate (i.e., the substrate 103). A flexible and optically transparent encapsulant 101 is then provided to encapsulate the light generating sources 102–102n on the substrate 103. Thus, the illumination unit 100 is both thin and flexible.

This thin and flexible illumination unit 100 can be used in a wide range of applications (e.g., photo-therapeutic, display, or lighting) where a compact, low voltage, rugged, and high efficiency light source is advantageous. For example, the illumination unit 100 can be employed to is build a motor vehicle lamp. In a further example, the illumination unit 100 can be a display panel or a photo-therapeutic unit. In one embodiment, the illumination unit 100 has a thickness of less than 8 mm.

In addition, as the whole illumination unit 100 is flexible, it can be bent to a desired shape or contour, i.e. it can be easily formed to follow the contour of a transparent part of a corresponding lamp. The illumination unit 100 in accordance with one embodiment of the present invention will be described in more detail below, also in conjunction with FIGS. 1–6.

Referring to FIGS. 1–6, the illumination unit 100 is shown to have the encapsulant 101, the solid-state light generating sources 102–102n, the flexible substrate 103, a thermal conductive tape 104, and a heat sink plate 105. Tracks (i.e., 121–126 in FIG. 4 or 141–145 in FIG. 6) are arranged on the substrate 103 and the substrate 103 is attached to the heat sink plate 105 via the tape 104.

Figure 3:
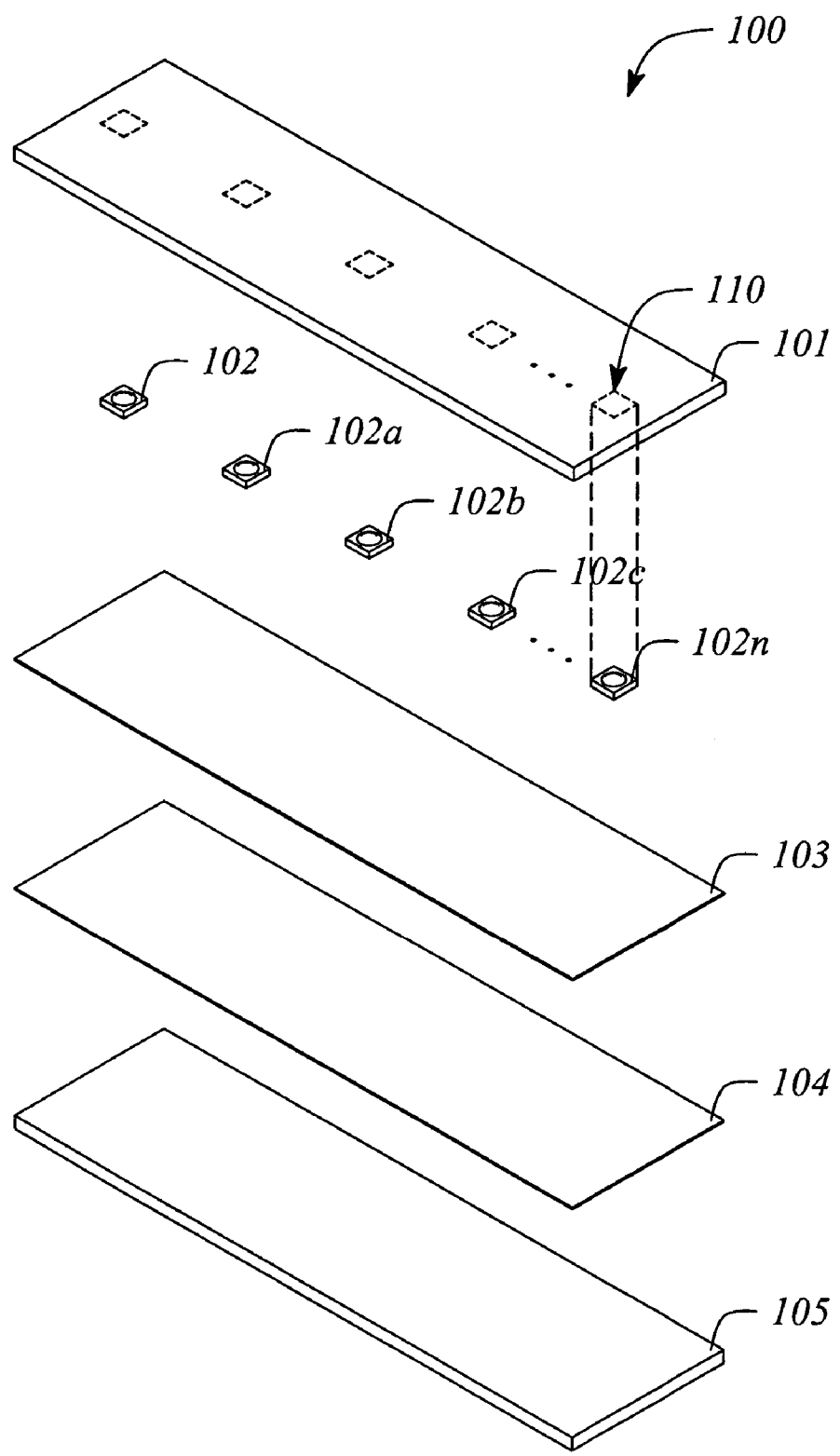
FIG. 3 shows an exploded view of the illumination unit of FIGS. 1–2.
Figure 4:
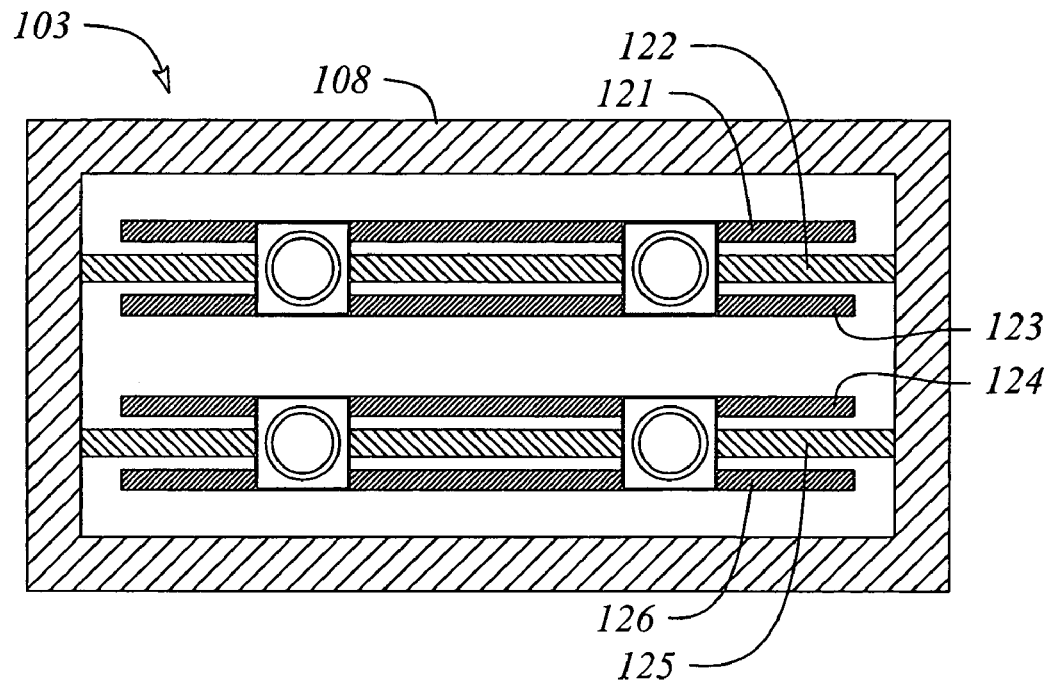
FIG. 4 is a plan view of a partial circuit layout on a flexible substrate of the illumination unit of FIGS. 1–3 in accordance with one embodiment of the present invention.
Figure 5:
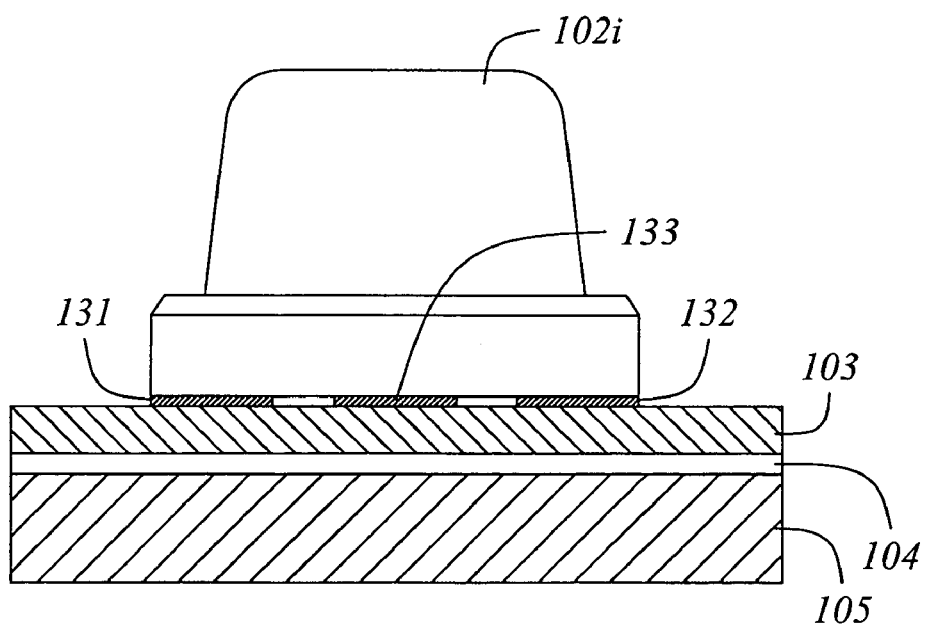
FIG. 5 is a cross-sectional view of a portion of the illumination unit of FIGS. 1–3, showing a surface-mounted solid-state light generating source on the tracks (both electrical and heat sink tracks) on the flexible substrate.
Figure 6:
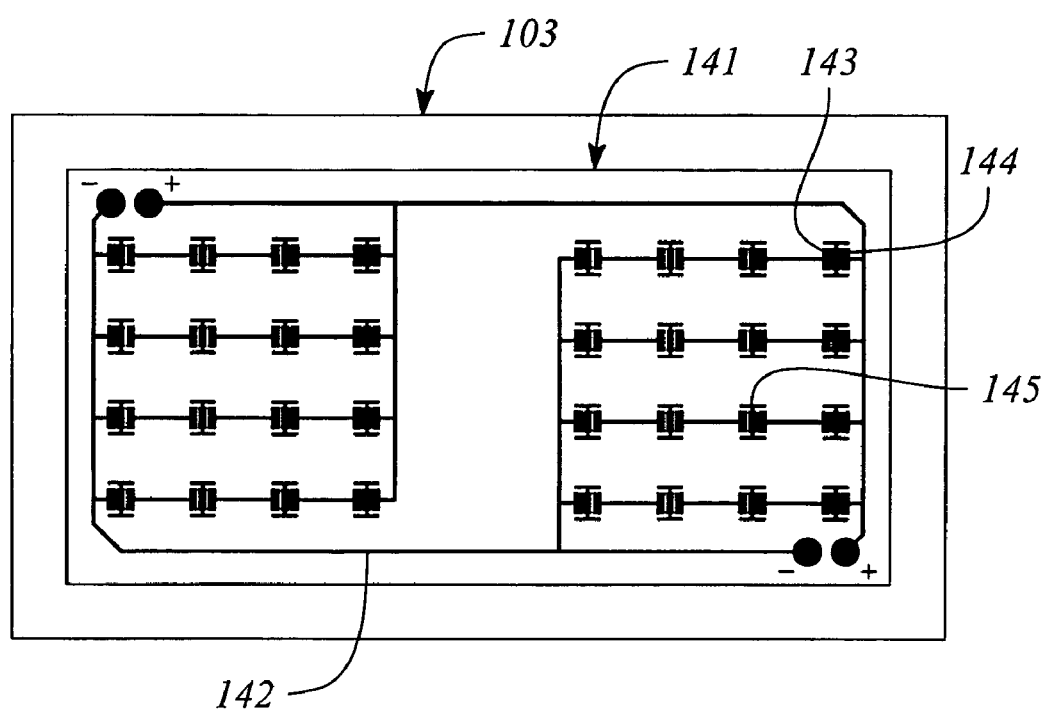
FIG. 6 is a plan view of a circuit layout on a flexible substrate of the illumination unit of FIGS. 1–3 in accordance with another embodiment of the present invention.

FIG. 3 shows the exploded view of the illumination unit 100 (without showing the tracks on the substrate 103). FIG. 3 also shows recesses (e.g., the recess 110) of the encapsulant 101 that receive the solid-state light generating sources (e.g., the light generating source 102n). In one embodiment, the recesses are formed when the encapsulant 101 is formed on the substrate 103 with the light generating sources 102–102n already mounted thereon. FIG. 4 shows the partial and illustrative layout of the tracks (i.e., the tracks 121–126) in accordance with one embodiment. FIG. 5 shows how each of the light generating sources 102–102n is mounted on the tracks (e.g., the tracks 121–126 of FIG. 4 or the tracks 141–145 of FIG. 6) on the flexible substrate 103 that is attached to the plate 105 via the adhesive tape 104. FIG. 6 shows the illustrative layout of the tracks (i.e., the tracks 141–145) in accordance with another embodiment.

The substrate 103 is a thin and flexible substrate. This means that the substrate 103 can be made of a film or foil material, and can be easily bent by hand. The substrate 103 may be made of an electrically insulating material.

In one embodiment, the flexible substrate 103 is made of a synthetic material (e.g., polyamide). A substrate made of the above-mentioned polyamide can provide for a sufficient electrical insulation as well as for a sufficient flexibility and strength. In another embodiment, the flexible substrate 103 is made of any electrically non-conductive but thermally conductive material (e.g., silicone or plastic sheet).

In one embodiment, the flexible substrate 103 is a flexible printed circuit board. In another embodiment, the flexible substrate 103 has a thickness of about 25.4 micrometers. Alternatively, the substrate 103 may have other thickness.

In addition, the illumination unit 100 may also include a heat sink frame 108 on the substrate 103. In one embodiment, the heat sink frame 108 surrounds the substrate 103. In another embodiment, the heat sink frame 108 is on the top and bottom surfaces of the substrate 103. In a further embodiment, the heat sink frame 108 is on one of the top and bottom surfaces of the substrate 103. The heat sink frame 108 may be made of metal.

The heat sink plate 105 that may serve both as heat sink and base support for the substrate 103. Alternatively, the illumination unit 100 may not include the heat sink frame 108 or the plate 105. In one embodiment, the plate 105 is a heat conducting metal plate or sheet attached to the substrate 103 via a thermally conductive adhesive. This means that the adhesive tape 104 can be thermally conductive adhesive. In another embodiment, the plate 105 is replaced with a heat conducting ceramic plate or sheet.

The flexible tracks (e.g., the tracks 121–126 in FIG. 4 or the tracks 141–145 in FIG. 6) are formed on the flexible substrate layer 103. The tracks include electrical tracks (e.g., the tracks 121, 123–124, and 126 in FIG. 4 or the tracks 141–144) and heat sink tracks (e.g., the tracks 122 and 125 in FIG. 4 or the track 145 in FIG. 6). The tracks may be arranged in a predetermined pattern on the substrate layer 103 in accordance with a desired light form and intensity.

Referring to FIG. 4, the tracks 121–126 include electrical tracks (e.g., the tracks 121, 123–124, and 126) and heat sink tracks (e.g., the tracks 122 and 125). Each of the electrical tracks is of a conductive material (e.g., metal). The tracks may be arranged in a predetermined pattern on the substrate layer 103 in accordance with a desired light form and intensity.

The electrical tracks (e.g., the tracks 121, 123–124, and 126) include at least an anode track or trace (e.g., the track 121 or 124) and a cathode track or trace (e.g., the track 123 or 126) extending parallel to each other. An anode terminal and a cathode terminal of a corresponding light generating source are attached to the corresponding tracks. Therefore, various light patterns having light spots and dark zones can be formed in accordance with the form of a light or lamp to be created.

In one embodiment, each of the tracks 121–126 is formed of a single material, such as a special metal. In another embodiment, each of the tracks 121–126 is formed of a multi-layer metal structure (not shown). In this embodiment, the track structure may include a copper layer, a nickel layer on top of the copper layer, and a gold layer on top of the nickel layer. Alternatively, some of the tracks may have the multi-layer structure while others may have a single metal layer.

In the multi-layer structure, the copper layer provides a good material for forming the circuit shape, the nickel layer helps preventing copper migration and provides additional strength, and the gold layer is preferable in wire bonding and both electrical and heat conduction and thereby is very suitable for having the light generating source's attached thereto. According to one embodiment, the copper layer is approximately 17.78 micrometer thick, the nickel layer is between 2.54 to 7.62 micrometer in thickness and the gold layer is at least 0.76 micrometer in thickness. The relatively thick copper layer provides for a sufficient cross-section for corresponding electrical energy supply, the nickel layer is kept relatively thinner in comparison to the copper layer. The gold layer is also kept thinner than the nickel layer in order to save costs.

The heat sink tracks or traces 122 and 125 are between the electrical tracks such that they are parallel to the corresponding anode and cathode tracks. The heat sink tracks 122 and 125 are connected to heat sink frame 108. With the frame 108, the heat from the light generating sources 102–102n is transported to the metal frame 108 via the corresponding heat sink tracks.

FIG. 6 shows the layout of the tracks in accordance with another embodiment. In FIG. 6, the tracks 141–145 include electrical tracks (e.g., the tracks 141–144) and heat sink tracks (e.g., the track 145). Each of the electrical tracks is of a conductive material (e.g., metal). The tracks may be arranged in a predetermined pattern on the substrate layer 103 in accordance with a desired light form and intensity.

The electrical tracks include a global anode track or trace 141 and a global cathode track or trace 142. The anode track 141 is connected to all anode terminal tracks (e.g., the terminal track 144) and the cathode track 142 is connected to all cathode terminal tracks (e.g., the terminal track 143). An anode terminal and a cathode terminal of a corresponding light generating source are attached to the corresponding tracks. Therefore, various light patterns having light spots and dark zones can be formed in accordance with the form of a light or lamp to be created.

FIG. 6 also shows heat sink tracks (e.g., the track 145). Each of the heat sink tracks is placed between a pair of terminal tracks. For example, the heat sink track 145 is placed between a pair of terminal tracks and the terminal track pair 143–144 sandwiches a heat sink track. In addition, each heat sink track is of the "□" shape. The heat sink tracks also are connected to the heat sink frame (not shown) that are the opposite side of the substrate 103 on which the heat sink tracks are not located. This connection can be made via heat sink via holes (also not shown in FIG. 6).

Referring to FIGS. 1–6, the solid-state light generating sources 102–102n of the illumination unit 100 are small surface mountable light generating sources and may include heat sink. The light generating sources 102–102n emit a broad-spectrum light. The light generating sources 102–102n are arranged (e.g., attached using the Surface Mounting Technology) on the flexible substrate 103 along the tracks (e.g., the tracks 121–126 in FIG. 4 or 141–145 in FIG. 6) and are electrically connected to the electrical tracks (e.g., the tracks 121, 123–124, and 126 in FIG. 4 or the tracks 141–144 in FIG. 6).

The solid-state light generating sources 102–102n can be implemented in various ways. Each of the solid-state light generating sources 102–102n can be a high power surface mountable light generating source. In one embodiment, each of the light generating sources 102–102n is a LED. In another embodiment, each of the light generating sources 102–102n is a laser diode. In a further embodiment, each of the light generating sources 102–102n is an organic LED. In a yet further embodiment, the light generating sources 102–102n can be a combination of LEDs, laser diodes, and organic LEDs.

When each of the light generating sources 102–102n is a LED or laser diode, the diode can be a diode chip or a diode package. If the diode is a diode package, it can be a PCB (Printed Circuit Board)-based diode package, a ceramic-based diode package, a leadframe-based diode package, a model-based diode package, or a metal-based diode package. Each of the diode packages has a built-in heat sink to enhance heat dissipation generated by a diode within the diode package. In one embodiment, the diode package also includes a reflector cup that reflects light and an optically designed dome shape to channel out the light at a predetermined viewing angle. Moreover, the diode within a diode package may be covered with luminescent material (e.g., phosphor) to convert the light generated by the diode in certain wavelength to light of other certain wavelength or wavelengths.

In one embodiment, each of the solid-state light generating sources 102–102n is a High Flux SMT (Surface Mounting Technology) LED manufactured by Agilent Technologies, Inc. of Palo Alto, Calif. (part number HSMZ-C4A0-TW001). This SMT LED is a PCB based LED package having a built-in heat sink copper pad at the bottom. Alternatively, other types of light generating sources can be used.

In another embodiment, each of the light generating sources 102–102n represents a color pixel that includes at least three light generating sources emitting in the red, green, and blue colors. The three light generating sources are closely packed to form the color pixel. In this case, the optical output intensity of the three colored light generating sources can be controlled to generate any desired color.

The flexible encapsulant 101 encapsulates the light generating sources 102–102n on the substrate 103 such that the illumination unit 100 is both thin and flexible. The encapsulant 101 is optically transparent and can be clear in color or tinted with a color (e.g., red). The encapsulant 101 is low thermal conductive.

In one embodiment, the encapsulant 101 is made of silicone. In this case, the silicon encapsulant can be biocompatible silicone. In another embodiment, the encapsulant 101 is an epoxy.

In one embodiment, the encapsulant 101 is body compatible. In another embodiment, the encapsulant 101 is not body compatible.

Moreover, the illumination unit 100 may include other electrical or electronic components (not shown) mounted on the substrate 103. These components may include resistors, capacitors, transistors, current regulators, and other integrated circuit chips. In one embodiment, when the solid-state light generating sources 102–102n are LEDs, the components may include LED drivers that are capable of controlling the brightness of LEDs in certain areas of the illumination unit 100.

Figure 2:
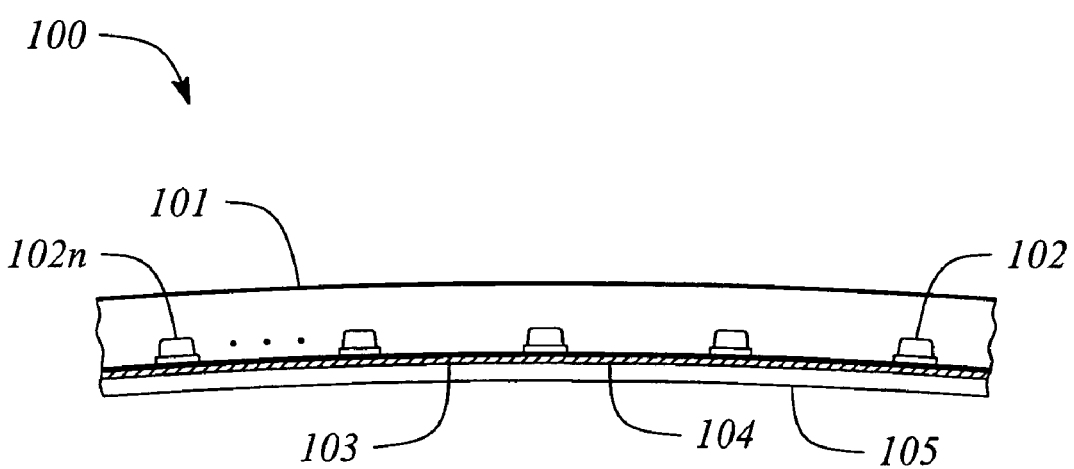
FIG. 2 shows a side cross-sectional view of the illumination unit as shown in FIG. 1.

Referring to FIGS. 1–3, the light generating sources 102–102n are mounted on and along the respective electrical tracks. Each of the light generating sources 102–102n is mounted in such a way that an anode terminal (not shown) of the light generating source is electrically connected to its corresponding anode track on the substrate 103, such as by soldering using screening technique or gluing, and a cathode terminal (not shown) of the light generating source is electrically connected to the corresponding cathode track on the substrate 103.

In one embodiment, each of the light generating sources 102–102n is attached to the corresponding electrical tracks using the Surface Mounting Technology (SMT). This makes the illumination unit 100 an SMT-light generating source-package-on-flexible-substrate assembly.

FIG. 5 shows a cross-sectional view of a portion of the illumination unit 100, showing how each of the light generating sources 102–102n is mounted on the tracks on the flexible substrate 103 that is attached to the plate 105 via the adhesive tape 104. As can be seen from FIG. 5, solder paste is deposited on the exact locations of the anode and cathode tracks 131–132 using, for example, screening techniques. Thermally conductive glue is also applied to the heat sink track 133 using, for example, dispensing technique. The light generating source 102i is then placed onto the respective electrical tracks 131–132, with the anode and cathode terminals of the light generating source 102i corresponding to the solder paste deposited on the anode and cathode tracks 131–132. The light generating source 102i is so placed such that its heat sink is in contact with the thermally conductive glue deposited on the heat sink track 133. The light generating source 102i is subsequently secured on the tracks 131–133 by re-flow soldering of the solder paste and curing the thermally conductive glue, respectively.

Referring back to FIGS. 1–3, the encapsulant 101 is coated on the substrate 103, encapsulating the light generating sources 102–102n. The encapsulant 101 is provided to prevent shortage of the electrical circuit and light generating sources 102–102n. The encapsulant 101 also provides mechanical and environmental protection to the light generating sources 102–102n. Besides, the encapsulant 101 also seals the heat dissipation path in order for the surface of the illumination unit 100 to remain at normal temperatures.

In one embodiment, the thickness of the plate 105 is about 0.64 mm (millimeter), the thickness of the substrate 103 is about 0.15 mm, the thickness of each of the light generating sources 102–102n is about 2.20 mm and the thickness of the encapsulant 101 is about 2.55 mm. This means that the assembled illumination unit 100 has a thickness of about 7.0 mm.

In the foregoing specification, the invention has been described with reference to specific exemplary embodiments thereof. The specification and drawings are, accordingly, to be regarded in an illustrative sense rather than a restrictive sense.

The invention claimed is:

1. An illumination unit, comprising:
   a thin and flexible substrate;
   a plurality of flexible electrical tracks formed on the flexible substrate;
   a plurality of solid-state light source packages arranged on the flexible substrate along the electrical tracks and being electrically connected to the electrical tracks, the light source packages having light generating sources, each light source package having at least one light generating source to generate light, a reflector cup to reflect the light, and an optically designed shape to channel out the light at a predetermined viewing angle; and
   a flexible and optically transparent encapsulant to encapsulate the light generating sources on the substrate without leaving any void such that the illumination unit is both thin and flexible.

2. The illumination unit of claim 1, wherein the encapsulant is made of biocompatible silicone.

3. The illumination unit of claim 1, wherein encapsulant is clear in color or tinted with dye.

4. The illumination unit of claim 1, wherein the encapsulant is of low thermal conductivity such that minimized heat is dissipated to the outer surface of the encapsulant.

5. The illumination unit of claim 1, wherein the light generating sources emit a broad-spectrum light.

6. The illumination unit of claim 1, wherein the light generating sources are selected from a group comprising fight emitting diodes, laser diodes, and organic light emitting diodes.

7. The illumination unit of claim 6, wherein the light source packages are selected from a group comprising a PCB (Printed Circuit Board) based diode package, a ceramic-based diode package, a leadframe-based diode package, a modal-based diode package, a metal-based diode package.

8. The illumination unit of claim 7, wherein the diode package includes a built-in heat sink to help dissipate heat generated by a diode within the diode package.

9. The illumination unit of claim 7, wherein the light source package further comprises a Light Emitting Diode chip that is covered with luminescent material.

10. The illumination unit of claim 1, wherein the flexible substrate is made of polyimide material.

11. The illumination unit of claim 1, wherein the flexible substrate is made of any electrically non-conductive but thermally conductive material.

12. The illumination unit of claim 1, further comprising a plurality of electronic components arranged on the flexible substrate.

13. The illumination unit of claim 12, wherein the electronic components are selected from a group comprising resistors, capacitors, transistors, current regulators, and drivers for light emitting diodes.

14. The illumination unit of claim 1, further comprising at least a heat sink track arranged on the substrate, and an anode track and a cathode track and the heat sink track is formed between the anode and cathode tracks.

15. The illumination unit of claim 14, further comprising a heat-conducting frame surrounding the substrate, the heat sink track being thermally connected to the frame.

16. The illumination unit of claim 15, further comprising a heat-conducting sheet attached with the substrate via a thermally conductive adhesive paste and in contact with the heat-conducting frame, wherein the heat-conducting sheet is made of one of metal or ceramic materials.

17. The illumination unit of claim 1, wherein the electrical tracks are multi-layer tracks that comprise a copper layer on the substrate layer, a nickel layer arranged over the copper layer, and a gold layer over the nickel layer.

18. The illumination unit of claim 1, wherein each of the light source packages is arranged on the substrate along the electrical tracks using a surface mount technology.

19. The illumination unit of claim 1, wherein the illumination unit is a display unit.

20. The illumination unit of claim 1, wherein the illumination unit is used to deliver light energy to the skin of a patient for phototherapy.

21. The illumination unit of claim 1, wherein the encapsulant is sufficiently thick such that the unit is flexible while providing adequate phototherapy to patient of the unit without harming the patient.

* * * * *

UNITED STATES PATENT AND TRADEMARK OFFICE
CERTIFICATE OF CORRECTION

| | |
|---|---|
| PATENT NO. | : 7,128,442 B2 |
| APPLICATION NO. | : 10/760763 |
| DATED | : October 31, 2006 |
| INVENTOR(S) | : Kian Shin Lee |

It is certified that error appears in the above-identified patent and that said Letters Patent is hereby corrected as shown below:

Column 7, Line 30, Claim 6, delete "fight" and insert -- light --.

Signed and Sealed this

Eighth Day of June, 2010

David J. Kappos
*Director of the United States Patent and Trademark Office*